(12) United States Patent
Bidney et al.

(10) Patent No.: US 6,337,100 B1
(45) Date of Patent: Jan. 8, 2002

(54) SUNFLOWER SEEDS WITH ENHANCED SATURATED FATTY ACID CONTENTS

(75) Inventors: Dennis L. Bidney, Urbandale; Sean Coughlan, Des Moines; Craig Hastings, Perry; Christopher J. Scelonge, Des Moines; Lijuan Wang, Johnston, all of IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/586,959

(22) Filed: Jun. 5, 2000

Related U.S. Application Data

(62) Division of application No. 08/624,845, filed on Mar. 25, 1996, now Pat. No. 6,084,164.

(51) Int. Cl.$^7$ .............................. A23D 7/00; A23D 9/00; A01H 5/00; A01H 5/10; C12N 15/82
(52) U.S. Cl. ....................... 426/601; 426/603; 426/606; 426/99; 554/1; 800/322; 800/281; 435/134
(58) Field of Search ................................. 426/601, 603, 426/606, 99; 554/1; 800/322, 281; 435/134

(56) References Cited

U.S. PATENT DOCUMENTS

| | | | | |
|---|---|---|---|---|
| 4,316,919 A | * | 2/1982 | Pelloso | 426/603 |
| 4,407,956 A | | 10/1983 | Howell | 435/172.3 |
| 4,536,475 A | | 8/1985 | Anderson | 435/172.3 |
| 4,684,611 A | | 8/1987 | Schilperoort et al. | 435/172.3 |
| 5,443,974 A | | 8/1995 | Hitz et al. | 435/172.3 |
| 6,084,164 A | * | 7/2000 | Bidney | 800/322 |

FOREIGN PATENT DOCUMENTS

| | | | |
|---|---|---|---|
| EP | 0 067 553 | | 12/1982 |
| EP | 0 275 069 | | 7/1988 |
| NE | 9 002 130 | | 4/1992 |
| WO | 85/01856 | | 5/1985 |
| WO | 91/13972 | | 9/1991 |
| WO | 91/18985 | | 12/1991 |
| WO | 93/11245 | | 6/1993 |
| WO | WO 95/20313 | * | 3/1995 |
| WO | 95/20313 | | 8/1995 |

OTHER PUBLICATIONS

Severn 1979 Bailey's Industrial Oil and Fat Products vol. 1, 4$^{th}$ edition John Wiley & Sons New York p. 511.*
Gunstone 1983 Lipids in Foods Chemistry, Biochemistry and Technology Pergamon Press New York p. 149, 151.*
Osouo 1995 Crop Science 35: 739–742.*
Steer 1990 J Sci Food Agric 51:11–26.*
Lajara 1990 JAOCS 67(10) 618–623.*
Robertson 1971 J Food Science 36: 873–876.*
Kabbaj et al.; "Expression D'Une Stearate Et D'Une Oleate Desaturases Chez Le Tournesol Normal Et A Haute Teneur En . . . "; OLC; vol. 3, No. 6; Nov. 1996; pp. 452–458.

Knutzon et al.; "Modification of Brassica Seed Oil by Antisense Expression of a Stearoyl–Acyl Carrier Protein Desaturase . . . "; Proceedings of the National Academy of Sciences; vol. 89; Apr. 1992; pp. 2624–2628.
Lightner et al.; "A Mutant of Arabidopsis with Increased Levels of Stearic Acid"; Plant Physiology; vol. 106; 1994; pp. 1443–1451.
Bafor et al.; "Properties of the Glycerol Acylating Enzymes in Microsomal Preparations from the Developing Seeds of Safflower (*Carthamus tinctorius*) and Turnip Rape (*Brassica campestris*) and their Ability to Assemble Cocoa–Butter Type Fats"; JAOCS; vol. 67, No. 4; Apr. 1990; pp. 217–225.
Tanksley et al.; "RFLP Mapping in Plant Breeding: New Tools for an Old Science"; Bio/Technology; vol. 7; Mar. 1989; pp. 257–264.
Osorio et al.; "Mutant Sunflowers with High Concentration of Saturated Fatty Acids in the Oil"; Crop Science; vol. 35; May–Jun. 1995; pp. 739–742.
Everett et al.; "Genetic Engineering of Sunflower (*Helianthus Annuus L.*)"; Bio/Technology; vol. 5; Nov. 1987; pp. 1201–1204.
Knutzon et al.; "Modification of Brassica Seed Oil by Antisense Expression of a Stearoyl–acyl Carrier Protein Desaturase Gene"; Proc. Natl. Acad. Sci. USA; vol. 89; Apr. 1989; pp. 2624–2628.
Ch'ng et al.; "Antisense RNA Complementary to 3'Coding and Noncoding Sequences of Creatine Kinase is a Potent Inhibitor of Translation in vivo"; Proc. Natl. Acad. Sci. USA; vol. 86; Dec. 1989; pp. 1006–1010.
Horsch et al., "A Simple and General Method for Transferring Genes into Plants", Science, vol. 227, (Mar. 1985), pp. 1229–1231.
Malone–Schoneberg et al., "Stable Transformation of Sunflower Using Agrobacterium and Split Embryonic Axis Explants", Plant Science 103, 1994, pp. 199–207.
Hood et al.; "New Agrobacterium Helper Plasmids for Gene Transfer to Plants"; Transgenic Research 2; 1993; pp. 208–218.
Bidney et al.; "Microprojectile Bombardment of Plant Tissues Increases Transformation Frequency by *Agrobacterium tumefaciens* "; Plant Molecular Biology; vol. 18; 1992; pp. 301–313.
Grubert et al.; "Vectors for Plant Transformation"; Methods in Plant Molecular Biology and Biotechnology; Glick and Thompson, ed.; 1993; pp. 89–119.

* cited by examiner

*Primary Examiner*—Carolyn Paden
(74) *Attorney, Agent, or Firm*—Foley & Lardner

(57) ABSTRACT

Antisense expression of a stearoyl-ACP desaturase gene in sunflower results in more than a four-fold increase in seed stearate, and can enhance palmitate content as well. Thus, sunflower oil containing over 40 percent saturated fatty acids can be produced, which is desirable in the context of various products, such as coating fat, margarine, soap and shortening.

5 Claims, 1 Drawing Sheet

SUNFLOWER SEEDS WITH ENHANCED SATURATED FATTY ACID CONTENTS

This Application is a Divisional of application Ser. No. 08/624,845, filed on Mar. 25, 1996, now U.S. Pat. No. 6,084,164.

FIELD OF THE INVENTION

This invention relates to transgenic sunflower plants that make seeds having high levels of saturated fatty acids. More specifically, the invention relates to antisense expression of a DNA segment having a sequence prepared from the sunflower stearoyl-ACP desaturase gene.

BACKGROUND OF THE INVENTION

Sunflower (*Helianthus annuus*) oil is a major edible oil worldwide. The oil component of sunflower seeds typically contributes about 80 percent of the value of a sunflower crop and is mostly used as a cooking medium. Sunflower oil also is employed as salad oil, as well as in the manufacture of margarine, soap, and shortening. Shortening is a fat, such as butter or lard, used to make cake or pastry light or flaky. These uses of sunflower oil however, are restricted by the amount of processing needed to modify the fatty acid composition of sunflower oil to eliminate the problems of rancidity, odor and texture.

Because of its high degree of unsaturation, sunflower oil is susceptible to oxidative changes during processing and storage as described, for example, by C. F. Adams, NUTRITIVE VALUE OF AMERICAN FOODS, Agricultural Handbook 456 (U.S. Department of Agriculture, 1975). The stability and flavor of sunflower oil is improved by hydrogenation, which chemically reduces fatty acid double bonds. But the need for this processing reduces the economic attractiveness of sunflower oil.

The principal fatty acids present in sunflower are the diunsaturated fatty acid linoleate, which comprises about 65 percent of the total, and the monounsaturated fatty acid oleate, which comprises about 25 percent of the total. Sunflower oil also comprises smaller amounts of saturated fatty acids, primarily palmitate and stearate. Palmitate constitutes about 4.5 percent to about 6.0 percent and stearate constitutes about 5.0 to about 6.0 percent of sunflower seed fatty acid.

These fatty acids are not present in the plant oil in their free form but primarily are found esterified to glycerol in the form of triglycerides. During plant oil fatty acid composition analysis, the triglycerides typically are broken down to release methyl derivatives of the constituent fatty acids.

Because of its fatty acid composition, unmodified sunflower oil is not well suited for the production of high quality margarines. One way to overcome this problem is to interesterify sunflower oil with another hydrogenated vegetable oil as suggested by Freier et al., *Ind. Aliment.* (Bucharest) 24: 604–07 (1973). Margarine manufacturers in the United States often interesterify sunflower oil with safflower or soybean oil, and then blend in a portion of hardened hydrogenated oil. Unfortunately, such processing leads to higher costs and health concerns due to the undesirable formation of trans fatty acids. If a sunflower oil contained a greater proportion of palmitate and stearate, then less processing would be needed to make margarine from it.

Oil can be converted into an edible fat for the confectionery industry. Unfortunately, fatty acid composition of conventional sunflower oil prevents the extensive use of this oil in the confectionery industry, for example, as a substitute for cocoa butter.

More than 2 billion pounds of cocoa butter, the most expensive edible oil, are produced annually in the world. The U.S. imports several hundred million dollar's worth of cocoa butter annually. The high prices and uncertain supplies of cocoa butter have encouraged the development of cocoa butter substitutes that have fatty acid compositions similar to cocoa butter.

The fatty acid composition of cocoa butter is typically 26 percent palmitate, 34 percent stearate, 35 percent oleate and 3 percent linoleate. The unique fatty acid composition of cocoa butter confers properties that make this edible fat eminently suitable for confectionery end-uses. Cocoa butter is hard and non-greasy at ordinary temperatures, and melts very sharply in the mouth. It is extremely resistant to oxidative reactions. For these reasons, producing sunflower oil with increased levels of stearate and palmitate, and reduced levels of unsaturated fatty acids could expand the use of sunflower as a cocoa butter substitute. Such a replacement of cocoa butter with sunflower oil would provide value to oil and food processors as well as reduce the foreign import of tropical oils.

Other traditional uses of saturated fat, such as raw material for the manufacture of soap and the coating of foods, could be filled by a sunflower oil having increased levels of stearate and palmitate. Animal fat is employed for these purposes because it contains a high level of saturated fatty acids. This gives animal fat a greater resistance to oxidation. Sunflower oil having increased levels of stearate and palmitate would similarly be less resistant to oxidation.

Coupled with traditional breeding, mutagenesis has been used to create sunflower varieties that have altered fatty acid compositions. One example of a sunflower variety made this way is Pioneer® hybrid 6661, which produces a seed storage oil having a fatty acid composition of about 85 percent oleate. Another example is a sunflower variety that bears seeds with a high stearate content as described by Osorio et al., *Crop Sci.* 35: 739–42 (1995).

The mutagenesis approach is severely limited in this context, however. It is unlikely to create a mutated variety in which a dominant or "gain-of-function" phenotype is created by a gene that is essential for plant growth or by a gene that exists in more than one copy. Also, slow and expensive traditional breeding techniques are required to introgress a mutation into an elite line. This problem stems from polygenic inheritance of genes that cause the desired oil composition.

The polygenic inheritance problem is evident in the high stearate lines created by Osorio et al. (1995), supra, in which seed stearate compositions changed through several generations. After three generations of inbreeding, sunflower seeds from two lines reported by Osorio et al. contained more than 10 percent stearate, less than 6 percent palmitate, and more than 13 percent oleate.

Recent molecular and cellular biology techniques offer the prospect of overcoming some of the limitations of the mutagenesis approach, including the need for extensive breeding. Particularly useful technologies are (a) seed-specific expression of foreign genes in transgenic plants, (b) use of antisense RNA to inhibit plant target genes in a dominant and tissue-specific manner, (c) transfer of foreign genes into elite commercial varieties of commercial oil crops such as sunflower, as described by Everett et al., *Bio/Technology* 5: 1201–04 (1987), and (d) use of genes as restriction fragment length polymorphism markers in a breeding program, which makes introgression of recessive traits into elite lines rapid and less expensive, as described by Tanksley et al., *Bio/Technology* 7: 257–64 (1989). But each of these technologies requires the identification and isolation of commercially important genes.

Some commercially important genes involved in fatty acid synthesis within the plant have been identified. For example, the biosyntheses of palmitate, stearate and oleate occur in the plastids by the interplay of three key "ACP track" enzymes: palmitoyl-ACP elongase, stearoyl-ACP desaturase and acyl-ACP thioesterase. Stearoyl-ACP desaturase introduces the first double bond on stearoyl-ACP to form oleoyl-ACP. This enzyme is pivotal and determines the degree of eighteen carbon length fatty acid unsaturation in vegetable oils.

Fatty acids synthesized in the plastid are exported as acyl-CoA to the cytoplasm. At least three different glycerol acylating enzymes: glycerol-3-P acyltransferase; 1-acyl-glycerol-3-P acyltransferase; and diacylglycerol acyltransferase incorporate acyl moieties from the cytoplasm into triglycerides during oil biosynthesis. These acyltransferases show a strong, but not absolute, preference for incorporating saturated fatty acids at positions 1 and 3 and monounsaturated fatty acid at position 2 of the triglyceride. Thus, altering the fatty acid composition of the acyl pool can drive by mass action, a corresponding change in the fatty acid composition of the oil. Furthermore, there is experimental evidence that, because of this specificity, given the correct composition of fatty acids, plants can produce cocoa butter substitutes. Bafor et al., *JAOCS* 67: 217–25 (1990).

Thus, one approach to alter the levels of stearate and oleate in sunflower oil entails modifying the levels of cytoplasmic acyl-CoA. This can be done genetically in two ways. First, altering the biosynthesis of stearate and oleate in the plastid may be effected by modulating the levels of stearoyl-ACP desaturase in seeds, either through overexpression or antisense inhibition of the stearoyl-ACP desaturase gene. A second approach involves converting stearoyl-CoA to oleoyl-CoA in the cytoplasm through the expression of stearoyl-ACP desaturase in the cytoplasm.

Antisense inhibition of a stearoyl-ACP gene can be achieved by placing a DNA segment in a cell such that it produces an RNA that is complementary to the stearoyl-ACP desaturase mRNA. For this strategy, a stearoyl-ACP desaturase gene is first isolated from which to make the DNA segment. It is preferred to isolate the actual gene(s) or cDNA(s) encoding stearoyl-ACP desaturase from sunflower, and not from another species. This is because antisense inhibition works best when there is a high-degree of complementarity between the antisense RNA and the targeted gene.

Antisense inhibition of plant stearoyl-ACP desaturase in canola has been reported by Knutzon et al., *Proc. Nat'l Acad. Sci. USA* 89: 2624–28 (1992); see also U.S. Pat. No. 5,443,974. These publications describe an increased level of stearate produced by antisense inhibition in seeds of canola and soybean, respectively. In the case of canola, transgenic seeds having the highest levels of stearate contained about 15 percent oleate, a four-fold reduction from the control value of about 60 percent oleate. In the case of soybean, the increased level of stearate was not accompanied by a decreased level of oleate. In both instances a cloned stearoyl-ACP desaturase from the respective plant species was used to construct transgenic DNA segments.

The expectation that antisense expression of the stearoyl-ACP desaturase gene only would affect the concentration of 18-carbon fatty acids was borne out by the data of Knutzon et al. (1992), supra, who found that an increase in stearate was not accompanied by an increase in palmitate. The experimental data set out in U.S. Pat. No. 5,443,974 also reveal an increase in stearate unaccompanied by an increase in palmitate.

Thus, the genetic alteration of plant stearoyl-ACP desaturase can affect the levels of 18-carbon fatty acids, but is not known to influence 16-carbon fatty acid metabolism. Yet an increase in both stearate and palmitate is desired for certain commercial uses, as summarized above. Accordingly, an approach to achieve a vegetable oil with a high stearate content and a high palmitate content would be a valuable addition to the art.

SUMMARY OF THE INVENTION

It is therefore an object of the present invention to provide sunflower oil that has an enhanced amount of stearate in relation to conventional sunflower oils, and that does not require extensive processing in producing margarine and confectioneries.

It also is an object of the present invention to provide sunflower oil that has an enhanced amount of both stearate and palmitate in relation to conventional sunflower oils.

It also is an object of the present invention to provide true breeding transgenic sunflower plant varieties that bear seeds having higher amounts of stearate and palmitate, compared to a wild-type variety.

It is a further object of the present invention to provide hybrid varieties of transgenic sunflower plants that bear seeds having higher amounts of stearate and palmitate, compared to a wild-type variety.

In accomplishing these and other objectives, there has been provided, in accordance with one aspect of the present invention, a sunflower plant comprising a chromosome that contains a DNA segment, the transcribed strand of which has a transcript that is complementary to endogenous stearoyl-ACP desaturase mRNA in the plant, such that stearoyl-ACP desaturase activity is reduced in the plant relative to wild type, wherein the plant provides seed that has a stearate content of between about 10 percent and about 40 percent of total seed fatty acid.

In accordance with another aspect of the present invention, there has been provided a sunflower seed produced by a plant comprising a chromosome that contains a DNA segment, the transcribed strand of which has a transcript that is complementary to endogenous stearoyl-ACP desaturase mRNA in the plant, such that stearoyl-ACP desaturase activity is reduced in the plant relative to wild type, wherein the seed has a stearate content of between about 10 percent and about 40 percent of total seed fatty acid. There also has been provided a product comprising of fatty acid from a sunflower seed produced by a plant according to the above aspect of the invention in a coating fat, margarine, soap, and shortening.

In accordance with yet another aspect of the present invention, there has been provided a sunflower variety that is true-breeding for a stearate content of between about 10 percent and about 40 percent of total seed fatty acid.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

Figure 1:
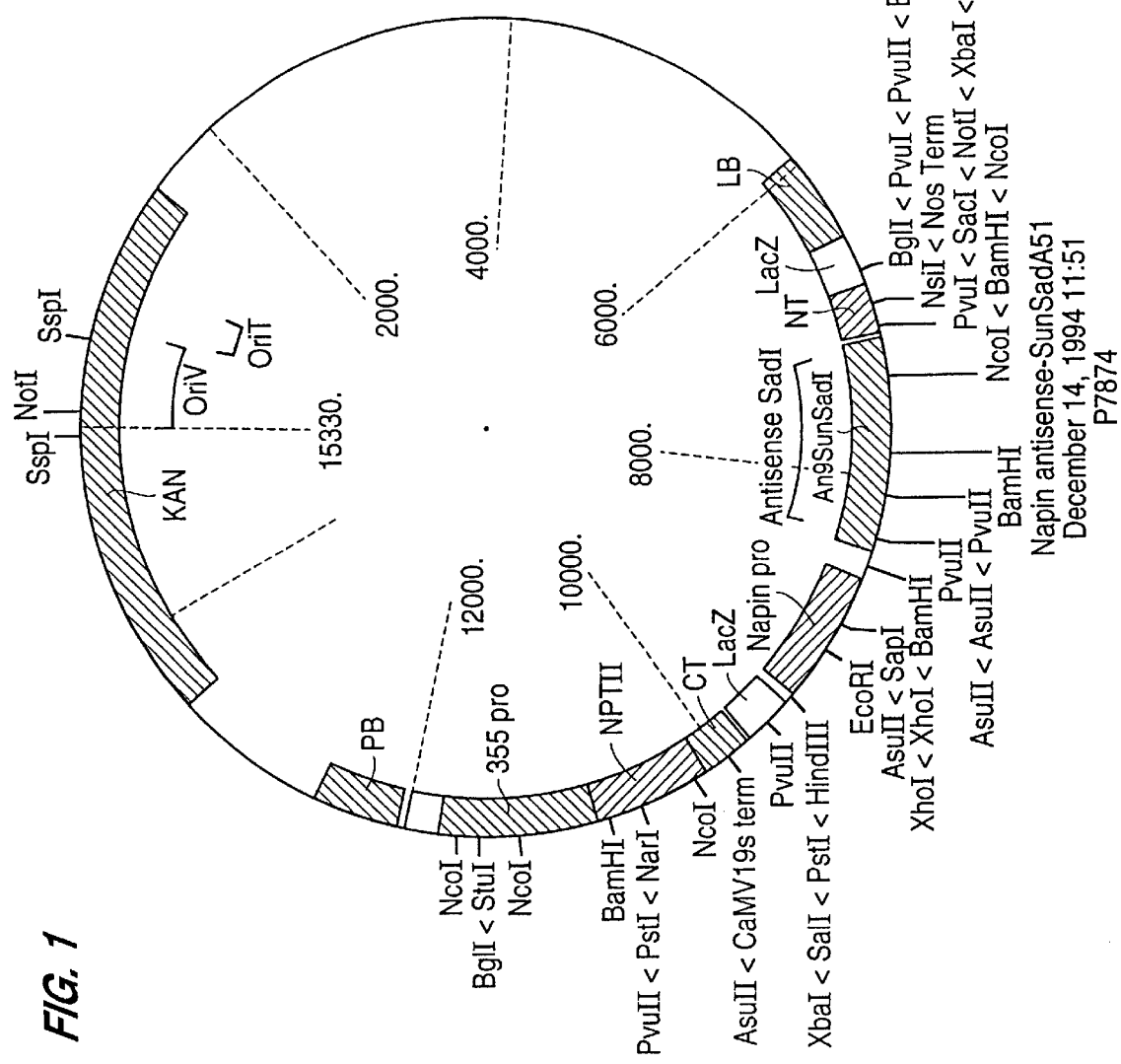
FIG. 1 is a schematic map of plasmid p7874, which can be used to introduce a DNA segment into sunflower.

It has been discovered that stearate content can be increased by antisense expression of sunflower stearoyl-ACP desaturase in sunflower. It also has been discovered that palmitate content can be increased by antisense expression of the sunflower stearoyl-ACP desaturase. According to the present invention, therefore, a method is presented for increasing the level of stearate by transgenic expression of a single DNA segment introduced into a sunflower variety. In a preferred embodiment, the levels of stearate and palmitate, respectively, are increased and the level of oleate is decreased by the transgenic expression of a single DNA segment.

The present invention allows for the production of a true-breeding sunflower variety of plants that bear seeds having higher amounts of stearate and palmitate, compared to a wild-type variety. The term "variety" refers to a group of plants within a species which share constant characters that separate them from the typical form and from other possible varieties within that species. While possessing at least one distinctive trait, a variety is also characterized by some variation between individuals within the variety, based primarily on the Mendelian segregation of traits among the progeny of succeeding generations.

A variety is considered "true breeding" for a particular trait if it is genetically homozygous for that trait to the extent that, when the true-breeding variety is self-pollinated, a significant amount of independent segregation of the trait among the progeny is not observed. In the present invention, the trait arises from transgenic expression of a single DNA segment introduced into a sunflower variety.

A transgenic hybrid variety having reduced stearoyl-ACP desaturase activity relative to wild-type can be created by hybridization with a variety that is inbred for antisense expression of the sunflower stearoyl-ACP desaturase gene.

In accordance with the present invention, a DNA molecule comprising a transformation/expression vector is engineered to include a sequence from a sunflower stearoyl-ACP desaturase gene. Extant knowledge concerning the sequence of plant stearoyl-ACP genes permits the isolation and cloning of a sunflower gene by standard methodology. Especially preferred is to use a cloned gene from another plant to screen a developing sunflower cotyledon cDNA library for a sunflower gene.

Once a stearoyl-ACP desaturase gene has been isolated, a copy of its sequence is placed into an expression vector by standard methods. The selection of an appropriate expression vector will depend upon the method of introducing the expression vector into host cells.

A typical expression vector contains: prokaryotic DNA elements coding for a bacterial replication origin and an antibiotic resistance gene to provide for the growth and selection of the expression vector in the bacterial host; a cloning site for insertion of the exogenous DNA sequence; eukaryotic DNA elements that control initiation of transcription of the exogenous DNA sequence, such as a promoter and an optional enhancer; and DNA elements that control the processing of transcripts, such as a transcription termination/polyadenylation sequence. The vector also could contain additional sequences that are necessary to allow for the eventual integration of the vector into a chromosome.

The selected DNA segment is cloned in reverse orientation into the vector to effect antisense expression of the stearoyl-ACP desaturase gene. "Antisense expression" is defined as the formation of a transcript from the introduced DNA segment that is complementary to stearoyl-ACP desaturase mRNA endogenous to the plant cell. The antisense expression of the DNA segment causes a reduction in stearoyl-ACP desaturase activity compared to activity levels characterizing the sunflower variety before transformation ("wild type").

Pursuant to the present invention, part or all of the stearoyl-ACP desaturase gene sequence, oriented such as to form a transcript that is complementary to endogenous stearoyl-ACP desaturase mRNA, may be used. Preferably the entire sequence is used, along with 3' non-coding sequences which are believed to participate in antisense inhibition. See Ch'ng et al., *Proc. Nat'l Acad. Sci. USA* 86: 10006–10 (1989).

The DNA segment of the present invention can be naturally formed or synthesized from a known sequence. The sequence may be obtained by making a cDNA from mRNA. The sequence may also be derived from a genomic DNA sequence. It is preferred to secure this sequence by making cDNA from mRNA that codes for the stearoyl-ACP desaturase protein.

Antisense expression of the DNA sequence is under the control of a promoter. Examples of suitable promoters are the promotor for the small subunit of ribulose-1,5-bisphosphate carboxylase, promoters from tumor-inducing plasmids of *Agrobacterium tumefaciens,* such as the nopaline synthase and octopine synthase promoters, and viral promoters such as the cauliflower mosaic virus (CaMV) 19S and 35S promoters or the figwort mosaic virus 35S promoter. The promoter can be constitutive or inducible.

Inducible antisense expression under the control of a promotor is preferred for synthesis of oil during seed maturation. Especially preferred is a "seed tissue-preferred" promoter, that is, a promoter that drives high expression of the heterologous DNA segment in seed tissue where control of genes that ate involved in seed metabolism is desired; some expression may occur in other parts of the plant. Examples of known seed tissue-preferred promoters include the soybean promoter of β-conglycinin, also known as the 7S protein, which drives seed-directed transcription (Bray, *Planta* 172: 364–370 (1987)), and seed-directed promoters from the zein genes of maize endosperm (Pedersen et al., *Cell* 29: 1015–26 (1982)).

Promoters of genes that are expressed during early embryogenesis and oil biosynthesis are particularly useful. The native regulatory sequences, including the native promotor of the stearoyl-ACP desaturase gene can be used following its isolation by a skilled artisan. Also suitable are heterologous promoters from other genes involved in seed oil biosynthesis, such as those for *Brassica napus* isocitrate lyase and malate synthase, as described by Comai et al. *Plant Cell* 1: 293–300, (1989); Arabidopsis ACP as described by Post-Beittenmiller et al., *Nucl. Acids Res.* 17: 1777 (1989); *B. napus* ACP as described by Safford et al., *Eur. J. Biochem.* 174: 287–95 (1988); and *B. campestris* ACP as described by Rose et al., *Nucl. Acids Res.* 15: 7197 (1987). Also, published sequences for the relatively abundant enoyl-ACP reductase and acetyl-CoA carboxylase proteins are available which can be employed in isolating, by conventional approaches, the promoters of these seed genes.

In addition to a suitable promoter, one or more enhancers are useful in the invention to increase transcription of the introduced DNA segment. The enhancer or enhancer-like element can be inserted into either the native stearoyl-ACP desaturase promoter or into other promoter constructs to provide higher levels of transcription. Examples of such enhancers include inter alia, viral enhancers like those within the 35S promoter, as shown by Odell et al., *Plant Mol. Biol.* 10: 263–72 (1988), and an enhancer from an opine gene as described by Fromm et al., *Plant Cell* 1: 977–84 (1989). If used with the 35S promoter, the enhancer element associated with that promoter is best placed in a direct repeat tandem arrangement with the CaMV 35S promoter. See Kay et al., *Science* 236: 1299 (1987).

Particularly preferred is a seed specific enhancer such as an enhancing DNA fragment isolated from the gene for the α subunit of β-conglycinin. This enhancer can effect a 40-fold seed specific enhancement to a constitutive promoter and is especially preferred. A skilled artisan can isolate this element and insert it into a promoter region upstream to the introduced DNA sequence to obtain seed-specific depression of stearoylACP desaturase.

The level of transgenic expression of the introduced DNA segment can be sustained by the stable maintenance of the DNA segment, along with any controlling promoters and enhancers, on a chromosome of the transgenic plant. Use of linked genes, with herbicide resistance in physical proximity to the introduced DNA segment, would allow for maintaining selection pressure on the transgenic plant population and for those plants where the DNA segment is not lost.

In accordance with the present invention, a transgenic plant is produced that contains a DNA molecule, comprised of elements as described above, which is integrated into its genome to give antisense expression of the stearoyl-ACP desaturase gene. In order to create such a transgenic plant, the expression vector containing the introduced DNA segment can be inserted into protoplasts; into intact tissues, such as immature embryos and meristems; into callus cultures or into isolated cells. Preferably, expression vectors are inserted into intact tissues. General methods of culturing plant tissues are provided, for example, by Miki et al., "Procedures for Introducing Foreign DNA into Plants," in METHODS IN PLANT MOLECULAR BIOLOGY AND BIOTECHNOLOGY 67–88 (CRC Press 1993).

Methods for introducing an expression vector into plant tissue include the direct infection or co-cultivation of plant tissue with *Agrobacterium tumefaciens*. Horsch et al., *Science* 227: 1229 (1985). Preferably, a disarmed Ti-plasmid is used as a vector for foreign DNA sequences. Most preferred is the use of Agrobacterium with split embryonic explants as described by Malone-Schoneberg et al., *Plant Science* 103: 199–207 (1994).

Although Agrobacterium is a preferred vector, other types of vectors can be used for transformation by procedures such as direct gene transfer, as described, for example, in PCT application WO 85/01856 and in European application No. 0 275 069; in vitro protoplast transformation, which is the subject of U.S. Pat. No. 4,684,611, for instance; plant virus-mediated transformation, illustrated in European application No. 0 67 553 and U.S. Pat. No. 4,407,956; and liposome-mediated transformation according to U.S. Pat. No. 4,536,475, among other disclosures.

Among the available direct transfer methods are microprojectile-mediated delivery, DNA injection, and electroporation. See, for example, Gruber et al., "Vectors for Plant Transformation," in METHODS IN PLANT MOLECULAR BIOLOGY AND BIOTECHNOLOGY (CRC Press 1993); Miki et al., "Procedures for Introducing Foreign DNA into Plants," loc. cit.; and Klein et al., *Bio/Technology* 10: 268 (1992).

in a preferred embodiment, the vector also contains a gene encoding a selection marker which is functionally linked to promoters that control transcription initiation. For a general description of plant expression vectors and reporter genes, see Gruber et al., "Vectors for Plant Transformation," in METHODS IN PLANT MOLECULAR BIOLOGY AND BIOTECHNOLOGY 89–119 (CRC Press, 1993).

The selection marker is used to recover transformed cells by either positive genetic selection or screening. Many of the commonly used positive selectable marker genes for plant transformation have been isolated from bacteria and code for enzymes that metabolically detoxify a selective chemical agent which may be an antibiotic or a herbicide. Other positive selection marker genes encode an altered target which is insensitive to the inhibitor.

A preferred selection marker gene for plant transformation is the neomycin phosphotransferase II (nptll) gene, isolated from Tn5, which confers resistance to kanamycin when placed under the control of plant regulatory signals. Fraley et al., *Proc. Nat'l Acad. Sci. USA* 80: 4803 (1983). Another useful selectable marker is the hygromycin phosphotransferase gene which confers resistance to the antibiotic hygromycin. Vanden Elzen et al., *Plan Mol. Biol.* 5: 299 (1985). Additional positive selectable markers genes of bacterial origin that confer resistance to antibiotics include gentamicin acetyl transferase, streptomycin phosphotransferase, aminoglycoside-3'-adenyl transferase and the bleomycin resistance determinant. Hayford et al., *Plant Physiol.* 86: 1216 (1988); Jones et al., *Mol. Gen. Genet.* 210: 86 (1987); Svab et al., *Plant Mol. Biol.* 14: 197 (1990); Hille et al., *Plant Mol. Biol.* 7: 171 (1986).

Other positive selectable marker genes for plant transformation are not of bacterial origin. These genes include mouse dihydrofolate reductase, plant 5-enolpyruvylshikimate-3-phosphate synthase and plant acetolactate synthase. Eichholtz et al., *Somatic Cell Mol. Genet.* 13: 67 (1987); Shah et al., *Science* 233: 478 (1986); Charest et al., *Plant Cell Rep.* 8: 643 (1990).

Another class of useful marker genes for plant transformation with the DNA sequence requires screening of presumptively transformed plant cells rather than direct genetic selection of transformed cells for resistance to a toxic substance such as an antibiotic. These genes are particularly useful to quantitate or visualize the spatial pattern of expression of the DNA sequence in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase, and chloramphenicol acetyltransferase. Jefferson, *Plant Mol. Biol. Rep.* 5: 387 (1987); Teeri et al., *EMBO J.* 8: 343 (1989); Koncz et al., *Proc. Nat'l Acad. Sci. USA* 84: 131 (1987); De Block et al., *EMBO J.* 3: 1681 (1984). Another approach to the identification of relatively rare transformation events has been use of a gene that encodes a dominant constitutive regulator of the *Zea mays* anthocyanin pigmentation pathway. Ludwig et al., *Science* 247: 449 (1990).

After screening, a transgenic plant is established by a conventional technique known to the skilled artisan. A preferred technique is to establish plantlets by in vitro grafting of regenerated sunflower shoots from split embryonic axis explants, as described by Paterson, *Am. J. Bot.* 71: 925–31 (1984).

Seeds from transgenic plants according to the present invention contain higher contents of stearate and palmitate and lower contents of oleate compared to seeds from non-transformed plants. Fatty acid contents of seeds can be determined by conventional techniques that are known to the skilled artisan. A preferred protocol entails subjecting seed extracts to methanolysis and then assaying the resultant fatty acid methyl esters by capillary gas chromatography as described in procedure CE1E-91 of OFFICIAL METHODS AND RECOMMENDED PRACTICES OF THE AMERICAN OIL CHEMISTRY SOCIETY (The American Oil Chemistry Society, 1995).

Stearate, palmitate and oleate contents are expressed in terms of a percent of "total seed fatty acid," i.e., the sum of 16:0, 16:1, 18:0, 18:1, 18:2, and 18:3 fatty acids in a seed sample. The amounts of each of these fatty acids are preferably determined simultaneously in an assay of a seed sample.

The highest levels of stearate and palmitate can be produced by antisense expression of the introduced DNA segment in a variety that already yields higher levels of saturated and/or monosaturated fatty acids compared to normal varieties. Preferred in this context is a variety that has been bred for high palmitate/high oleate seed contents such as Pioneer® hybrid variety 6661. Especially preferred is a variety that has a seed oil comprising from 15 to 20 percent palmitate and about 70 percent oleate fatty acid. Antisense expression of the introduced DNA segment in such a variety would result in sunflower oil comprised of at least 20 percent palmitate and at least 30 percent stearate.

A genetic map can be generated for transgenic plants having seeds with desireable fatty acid compositions. The map can be derived primarily via conventional RFLP and PCR analysis, to identify the approximate chromosomal location of the integrated DNA segment. For exemplary methodologies in this regard, see Glick & Thompson in METHODS IN PLANT MOLECULAR BIOLOGY AND BIOTECHNOLOGY 269–84 (CRC Press, 1993). Map information concerning chromosomal location is useful for proprietary protection of a subject transgenic plant. If unauthorized propagation is undertaken, and crosses are made with other germplasm, the map of the integration region can be compared to similar maps for suspect plants, to determine if the latter have a common parentage with the subject plant. Map comparisons would involve hybridizations, RFLP, PCR and sequencing, all of which are conventional techniques.

The present invention is further described by reference to the following, illustrative example.

Transformation of Sunflower Plant to Produce an Oilseed Having a High Concentration of Saturated Fatty Acids A. Isolation and cloning of a sunflower stearoyl-ACP gene A developing sunflower (SMF-3) cotyledon cDNA library (10–20 days after pollination) was constructed in UNIZAP® (Stratagene Inc., La Jolla, Calif.) from poly A+selected RNA. The amplified library was screened with a castor cDNA stearoyl-ACP desaturase supplied by C. Somerville of Michigan State University (East Lansing, Mich.). Positively hybridizing clones were purified to homogeneity by rescreening. The inserts were rescued into p Bluescript SK. The largest insert was about 1.5 kilobases long and was fully sequenced in both directions.

Disarmed *A. tumefaciens* strain EHA105, described by Hood et al., *Transgenic Research* 2: 208–18 (1993) was transformed with binary T-DNA plasmid PHP 158 and used in all transformation experiments. See Bidney et al., *Plant Mol. Biol.* 18: 301–13 (1992), and Malone-Schoneberg et al., *Plant Science* 103: 199–207. The full-length cDNA was cloned in the reverse orientation into the vector downstream of a napin promotor from the napin gene from *Brassica napus*. This promotor allows strong expression of a cis-controlled gene sequence during seed maturation. The final construct, designated p7874 (see FIG. 1), contained a single 35S promoter and a NPTII gene to confer kanamycin resistance.

B. Explant preparation, transformation and transgenic plant recovery

Mature sunflower seeds of Pioneer® hybrid 6440 or research selection SMF-3 were dehulled and surface sterilized for 30 min in a 20 percent Chlorox® bleach solution with the addition of two drops of Tween 20 per 50 ml of solution. Seeds were rinsed twice with distilled water.

Seeds were imbibed in distilled water for 60 min following the, surface sterilization procedure. The cotyledons of each seed were broken off to produce a clean fracture at the plane of the embryonic axis. Following excision of the root tip, the explants were bisected longitudinally between the primordial leaves. The two halves were placed cut surface up on GBA medium consisting of Murashige and Skoog mineral elements, Shepard's vitamin additions, 40 mg/l adenine sulfate, 30 g/l sucrose, 0.5 mg/l 6-benzyl-aminopurine, 0.25 mg/l indole-3-acetic acid, 0.1 mg/l gibberellic acid pH 5.6, and 8 g/l Phytagar.

Thirty to forty explants at a time were placed in a circle at the center of a 60×20 mm plate for microprojectile bombardment. Approximately 4.7 mg of 1.8 um tungsten microprojectiles were re-suspended in 25 ml of sterile TE buffer (10 mM Tris-Cl, 1 mM EDTA pH 8) and 1.5 ml aliquots were used per bombardment. Each plate was bombarded twice through a 150 um Nytex screen placed 2 cm above the samples in a PDS 1000® particle acceleration device.

Plasmid p7874 was introduced into *Agrobacterium tumefaciens* via freeze thawing as described by Holsters et al., *Mol. Gen. Genet.* 163: 181–7 (1978). Bacteria used for transformation were grown overnight (28° C. and 100 RPM continuous agitation) in liquid YEP medium (10 g/l yeast extract, 10 g/l Bactopeptone and 5 g/l NaCl, pH 7.0) in the presence of kanamycin. Bacterial cultures growing in log phase were used to make a suspension with an $OD_{600}$) of 0.6 in incubation medium comprised of 12.5 mM 2-(N-morpholino) ethanesulfonic acid, MES, 1 g/l $NH_4Cl$ and 0.3 g/l $MgSO_4$ at pH 5.7.

Freshly bombarded explants were placed in an Agrobacterium suspension, mixed and left undisturbed for 30 min. The explants were then transferred to GBA medium with co-cultivated cut surfaces down at 26° C. for 18-h days. After 3 days of co-cultivation, the explants were transferred to 374B (GBA medium lacking growth regulators and having a reduced sucrose level of 1 percent) supplemented with 250 mg/l cefotaxime and 50 mg/l kanamycin sulfate. The explants were cultured for 2–5 weeks on the supplemented medium and then transferred to fresh 374B medium lacking kanamycin for 1–2 weeks of continued development. Explants with differentiating, antibiotic resistant areas of growth that had not produced shoots suitable for excision were transferred to GBA medium containing 250 mg/l cefotaxime for a second 3-day phytohormone treatment. Leaf samples from green, kanamycin-resistant shoots were assayed for the presence of NPTII activity. Those shoots that failed to exhibit the presence of NPTII were discarded.

NPTII positive shoots were grafted to Pioneer® hybrid 6440 in vitro grown sunflower seedling rootstock. Surface sterilized seeds were germinated in 48-0 medium (half strength Murashige and Skoog salts, 0.5 percent sucrose, 0.3 percent gelrite pH 5.6) and grown under the conditions described for explant culture. The upper portion of each seedling was removed, a 1-cm verticle slice was made in each hypocotyl, and each transformed shoot was inserted into a cut. The entire area of each prepared graft was wrapped with parafilm to secure each shoot. Grafted plants were transferred to soil following 1 week of in vitro culture. Grafts in soil were maintained under high humidity conditions, followed by a slow acclimatization to a greenhouse environment.

Transformed sectors of $T_0$ plants (parental generation) maturing in the greenhouse were identified by NPTII analysis of leaf extracts. Transgenic seeds harvested from NPTII-positive $T_0$ plants were identified by first germinating each seed and establishing plants in the greenhouse, then performing NPTII analysis of T1 leaf tissue. The initial fatty acid analysis was done on cotyledon pieces of T2 seed populations obtained from transgenics as confirmed by T1 leaf NPTII assay. The seed assays could be used for segregation analysis of selfed progeny populations.

NPTII was detected by the Neomycin Phosphotransferase II ELISA kit provided by Agdia Inc. (catalog #F730; Elkhart, Ind.). Tissue extracts in MWBI buffer (MES, NaCl, Tween-20, pH 7.2) were incubated in microtiter plate wells coated with rabbit anti-NPTII IgG antibodies. Bound NPTII for the extracts was detected by the addition of peroxidase conjugated rabbit anti-NPTII specific IgG antibodies followed by the development of a hydrogen peroxide based calorimetric reaction. Absorbance of the sample wells at 450 nm was used to quantitate NPTII amounts in the original extracts by comparison with NPTII standard curves derived from the same assay conditions. Total protein in each assayed sample was determined by the Bradford method. See Bradford, Anal. Biochem. 72: 248–54 (1976).

DNA was isolated from immature leaves of greenhouse grown sunflower plants by a modified hexadecyltrimethylene ammonium bromide (CTAB) extraction protocol. For each sample, leaf tissue (2 g) was frozen in liquid nitrogel, ground with a mortar and pestle, and mixed into 9 ml of CTAB extraction buffer (200 ml of 1M Tris pH 7.5, 20 gm CTAB, 81.76 gm NaCl, 40 ml 0.5M EDTA pH 7.5, $H_2O$ to a final volume of 2l). Five ml of chloroform/octanol (24:1) are added and mixed. The aqueous layer obtained after centrifugation is removed and 11 ml of CTAB precipitation buffer (100 ml of 1M Tris pH 7.5, 40 ml 0.5M EDTA pH 7.5, 20 gm CTAB, $H_2O$) to a final volume of 2l) are added. The pellet obtained following centrifugation is dissolved in 2 ml of 100 mM Tris pH 7.5, 10 mM EDTA pH 7.5 and 0.7M NaCl. Five ml of 95–100% EtOH are added to precipitate the DNA. The DNA is removed by a hooked glass pasture pipette and first washed in 1 ml of 76% EtOH, 0.2M sodium acetate and then rinsed in 1 ml of 76% EtOH, 10 mM ammonium acetate. The pellet is resuspended in TE buffer to an approximate concentration of 0.25 ug/ul.

DNA (about 10 mg) was digested with 5–10 units of XbaI/mg DNA at 37 degrees C. for 3 hours. Samples were subjected to electrophoresis on a one percent agarose gel and transferred onto nylon membranes for hybridization analysis as described by Southern, *J. Mol. Biol.*, 98: 503–17 (1975). XbaI drops out the Napin::antisense SADI gene of p7874. The NPTTI gene was shown to be located between the XbaI site and the T-DNA right border sequence. See map of plasmid p7874 in FIG. 1. T-DNA junctions with plant genomic DNA at the right border were detected using XbaI digestion followed by hybridization to a radiolabeled probe generated by random prime labeling of the NPTII fragment as described by Feinberg & Vogelstein, *Anal. Biochem.*, 137: 266–7 (1984).

DNA's from individual progeny of T0 transgenic plants were assayed for the presence of antisense SADI DNA. Plant DNA was digested wi XbaI, transfered. to hybond-N membranes, and then probed with radioactively labeled 2.3 kb Napin-AntisunsadI gene generated by random prime labeling of the antisense SADI fragment as described by Feinberg & Vogelstein, loc. cit. The antisense DNA sequence was detected in the progeny. only one band was found from hybridization with the NPTII probe, therefore, the antisense DNA segment was present in only one copy.

C. Seeds produced by transgenic plants

Eight plants were transformed. Transgenic seeds from transformed plants contained higher levels of stearate and lower levels of oleate compared to seeds from untransformed plants. Some seed samples had a fatty acid composition that was at least 35 percent stearate.

An inverse relationship was found between stearate and oleate fatty acid compositions of seed oil from transgenic plants. Seed fatty acid compositions that were highest in stearate contained less than 5 percent oleate.

The relationship between seed stearate and palmitate fatty acid levels was positive and significant. Seeds having fatty acid compositions of more than 30 percent stearate also contained an average of 7.8 percent fatty acid as palmitate, for an average saturated fatty acid content of more than 40 percent. Control, non-transgenic seeds contained an average of less than 5.5 percent fatty acid as palmitate.

What is claimed is:

1. A product from a sunflower seed produced by a plant of a true breeding variety, said plant comprising a chromosome that contains a DNA segment, the transcribed strand of which has a transcript that is complementary to endogenous stearoyl-ACP desaturase mRNA in said plant, such that stearoyl-ACP desaturase activity is reduced in said plant relative to wild type, wherein said product comprises fatty acid and has an average saturated fatty acid content of more than 40%.

2. A product according to claim 1 which is a coating fat comprising said fatty acid.

3. A product according to claim 1 which is a margarine comprising said fatty acid.

4. A product according to claim 1 which is a soap comprising said fatty acid.

5. A product according to claim 1 which is a shortening comprising said fatty acid.

* * * * *